(12) United States Patent
Nekozuka et al.

(10) Patent No.: US 7,530,991 B2
(45) Date of Patent: May 12, 2009

(54) VERTEBRAL BODY DISTANCE RETAINER

(75) Inventors: Yoshio Nekozuka, Hokkaido (JP); Kazuya Oribe, Tokyo (JP); Hiroshi Takamido, Aichi-ken (JP)

(73) Assignee: Showa Ika Kohgyo Co., Ltd., Aichi-Ken (JP)

( * ) Notice: Subject to any disclaimer, the term of this patent is extended or adjusted under 35 U.S.C. 154(b) by 349 days.

(21) Appl. No.: 10/359,176

(22) Filed: Feb. 6, 2003

(65) Prior Publication Data

US 2003/0153915 A1    Aug. 14, 2003

(30) Foreign Application Priority Data

Feb. 8, 2002    (JP)    ............... 2002-032752

(51) Int. Cl.
*A61B 17/70*    (2006.01)

(52) U.S. Cl. .................. 606/248; 606/250; 606/252

(58) Field of Classification Search .................. 606/60, 606/61, 73, 258, 252, 261, 279, 248, 250, 606/86 A
See application file for complete search history.

(56) References Cited

U.S. PATENT DOCUMENTS

| | | | |
|---|---|---|---|
| 4,289,123 A | | 9/1981 | Dunn |
| 4,978,357 A | * | 12/1990 | Goymann et al. ......... 623/22.4 |
| 5,522,816 A | * | 6/1996 | Dinello et al. ................ 606/61 |
| 5,603,714 A | * | 2/1997 | Kaneda et al. ................ 606/61 |
| 5,702,452 A | | 12/1997 | Argenson et al. |
| 5,725,582 A | * | 3/1998 | Bevan et al. ................... 606/61 |
| 5,947,966 A | * | 9/1999 | Drewry et al. ................ 606/61 |
| 6,283,967 B1 | * | 9/2001 | Troxell et al. ................ 606/61 |
| 6,432,108 B1 | * | 8/2002 | Burgess et al. ............... 606/61 |
| 6,585,738 B1 | * | 7/2003 | Mangione et al. ............ 606/61 |
| 6,875,211 B2 | * | 4/2005 | Nichols et al. ................ 606/61 |

FOREIGN PATENT DOCUMENTS

| | | |
|---|---|---|
| FR | 2704420 | 11/1994 |
| FR | 2738143 | 3/1997 |
| JP | 8-252264 | 10/1996 |
| JP | 2000-501624 | 2/2000 |
| WO | WO 00/59387 | 10/2000 |
| WO | WO 01/03570 | * 1/2001 |
| WO | 01/91657 | 12/2001 |

OTHER PUBLICATIONS

English language Abstract JP 8-252264 (Oct. 1, 1996).

* cited by examiner

*Primary Examiner*—Pedro Philogene
(74) *Attorney, Agent, or Firm*—Greenblum & Bernstein, P.L.C.

(57) ABSTRACT

A vertebral body distance retainer comprises a retainer member including engaging portions to be engaged with a pair of rods provided on a plurality of adjacent vertebral bodies and abutting portions capable of freely abutting on spinous processes of the adjacent vertebral bodies, and fixing screws which fix the rods being engaged with the engaging portions. The vertebral body distance retainer is disposed between the spinous processes each existing on the adjacent vertebral bodies, so that the distance between the spinous processes can be retained constant.

3 Claims, 3 Drawing Sheets

VERTEBRAL BODY DISTANCE RETAINER

BACKGROUND OF THE INVENTION

1. Field of the Invention

The present invention relates to a vertebral body distance retainer for constantly retaining a distance between spinous processes by disposing the retainer between spinous processes each existing on adjacent vertebral bodies. More specifically, the present invention relates to a vertebral body distance retainer capable of effectively controlling displacement of the vertebral bodies.

2. Description of the Related Art

A device shown in FIG. 1A and FIG. 1B is known as a proposed vertebral body distance retainer for retaining a distance between spinous processes, which is disposed between the spinous processes each existing on adjacent vertebral bodies. This vertebral body distance retainer 101 has the constitution in which control plates 105 each protruding outward are provided on both end portions of a U-shaped retainer member 103.

As shown in FIG. 1B, the vertebral body distance retainer 101 has the constitution in which the retainer member 103 is disposed between spinous processes 109 each existing on adjacent vertebral bodies 107 and the control plates 105 provided on the retainer member 103 are engaged with side surfaces of the spinous processes 109.

SUMMARY OF THE INVENTION

However, since the proposed distance retainer 101 is designed to be simply placed between the spinous processes 109, the distance retainer 101 has a problem in terms of stability upon fixing a position between the vertebral bodies.

The present invention has been made in consideration of the above problems. It is an object of the present invention to provide a vertebral body distance retainer capable of tightly fixing adjacent vertebral bodies to achieve high stability.

To achieve the object described above, the present invention provides a vertebral body distance retainer, comprising: a retainer member including engaging portions to be engaged with a pair of rods provided on a plurality of adjacent vertebral bodies, and abutting portions capable of freely abutting on spinous processes of the adjacent vertebral bodies; and fixing screws which fix the rods, the rods being engaged with the engaging portions, wherein the vertebral body distance retainer is disposed between the spinous processes each existing on the adjacent vertebral bodies, so that the distance between the spinous processes can be retained constant.

BRIEF DESCRIPTION OF THE DRAWINGS

The invention will now be described with reference to the accompany drawings wherein.

DETAILED DESCRIPTION OF THE PREFERRED EMBODIMENT

Hereinafter, description will be made of embodiments of the present invention with reference to the drawings.

Figure 1A:
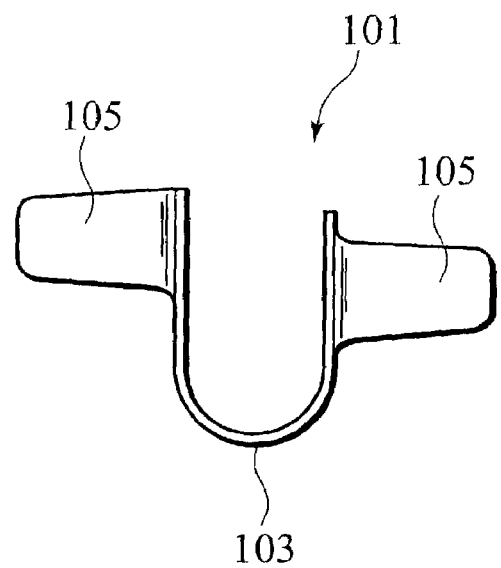
FIG. 1A and FIG. 1B are schematic views showing a structure of a proposed vertebral body distance retainer.
Figure 1B:
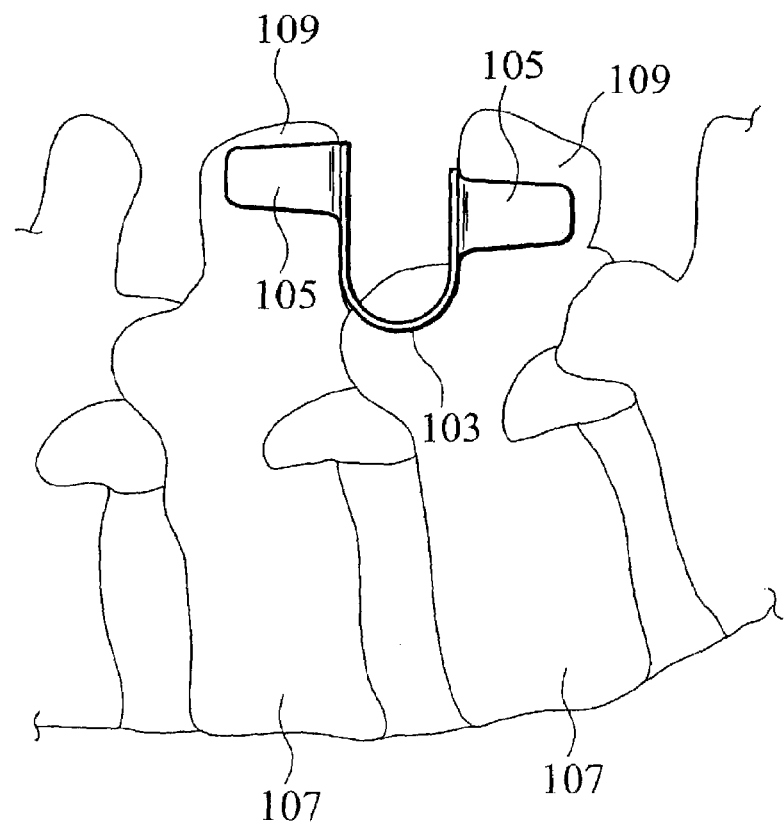
Figure 2:
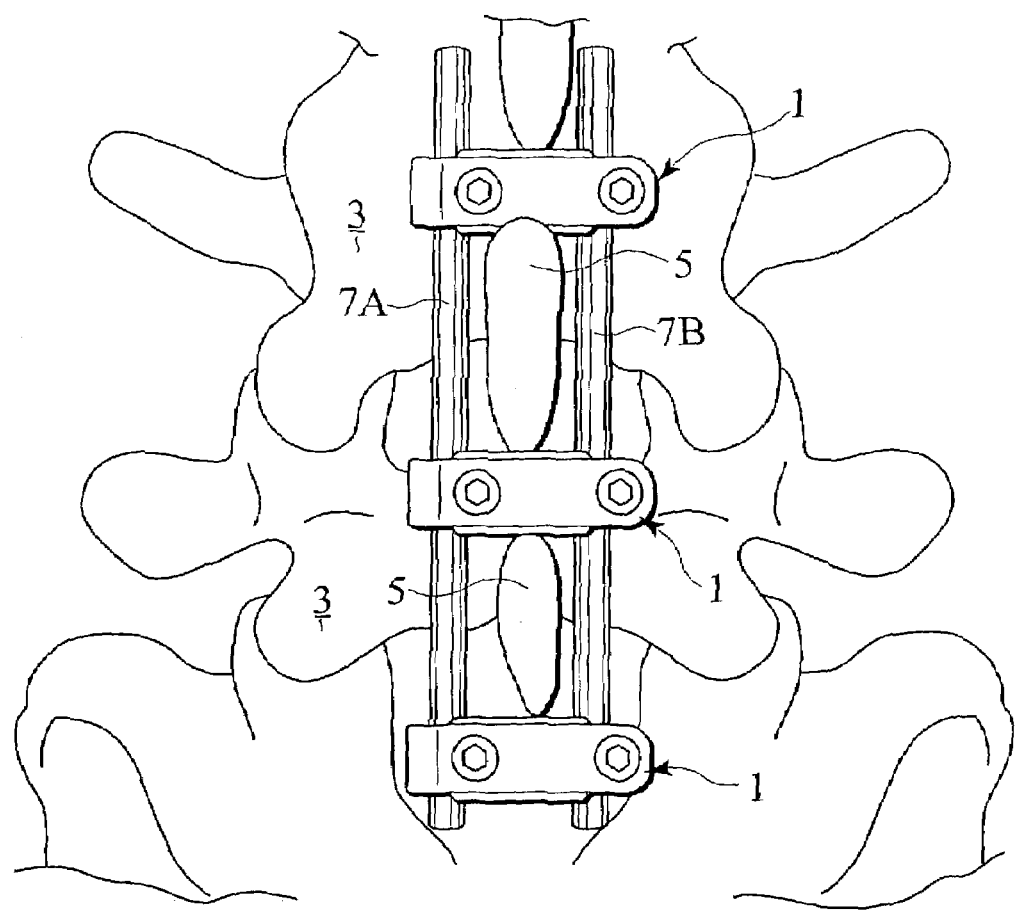
FIG. 2 is a schematic view showing a structure of a vertebral body distance retainer according to an embodiment of the present invention.

As shown in FIG. 2, a vertebral body distance retainer 1 according to an embodiment of the present invention is disposed and used between spinous processes 5 each existing on adjacent vertebral bodies 3. Upon fixation thereof, the vertebral body distance retainer 1 is fixed to a pair of rods 7A and 7B, which are disposed so as to sandwich the spinous processes 5.

FIG. 2 shows a constitution example in which the vertebral body distance retainers 1 are each fitted to both ends of the pair of rods 7A and 7B so that the rods 7A and 7B are fixed by allowing the vertebral body distance retainers 1 to abut respectively on the spaced spinous processes 5. However, as the constitution for fixing the pair of rods 7A and 7B, it is also possible to apply a constitution in which a plurality of implants such as screws are each screwed and fixed to the spaced vertebral bodies 3 so that the both end portions of the rods 7A and 7B are fixed to the plurality of implants. Otherwise, it is also possible to apply a constitution in which a hook is provided on one end of each of the rods 7A and 7B so that each of the hooks is hanged and fixed on a pedicle of vertebral arch existing on the vertebral body. It is possible to apply various types of constitutions for fixing the pair of rods 7A and 7B as appropriate.

Figure 3A:
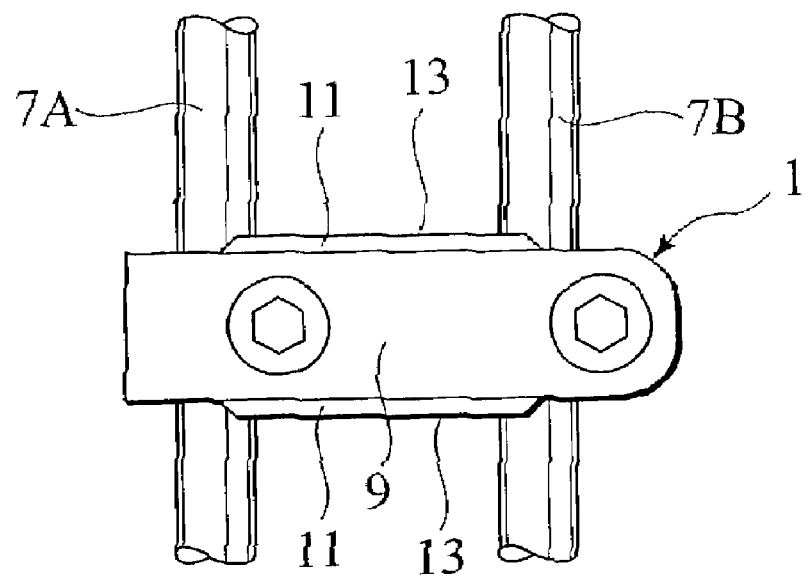
FIG. 3A is a top plan view showing a structure of a vertebral body distance retainer according to an embodiment of the present invention.
Figure 3B:
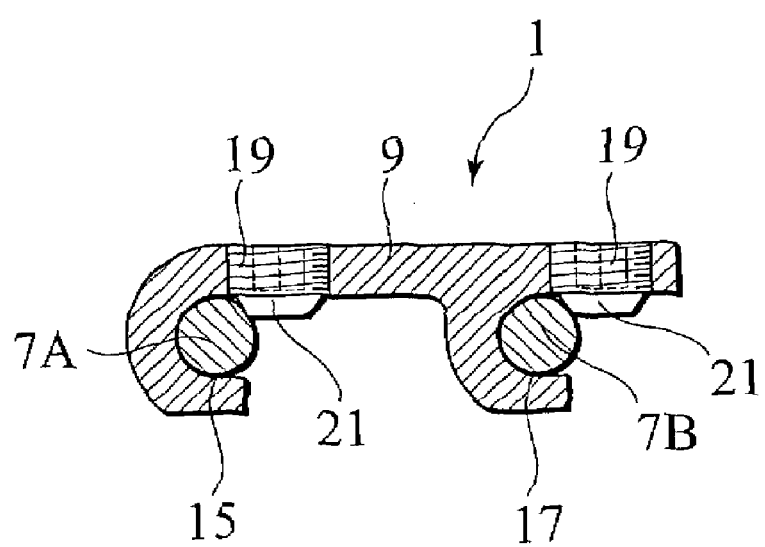
FIG. 3B is a cross-sectional view showing a structure of a vertebral body distance retainer according to an embodiment of the present invention.

As shown in FIG. 3A and FIG. 3B, the vertebral body distance retainer 1 includes a plate type retainer member 9. On both ends in the width direction of the retainer member 9, abutting portions 11 that can freely abut on the spinous processes 5 are formed. Moreover, outer edges 13 can bite into the spinous processes 5. Additionally, as illustrated in FIG. 3A, a first distance $D_1$ extending generally perpendicular between respective edges of the oppositely projecting sharp blades may be larger than a second distance $D_2$ extending generally perpendicular between the generally parallel side surfaces.

Engaging portions 15 and 17 for engaging with the pair of rods 7A and 7B are provided on a lower side of the retainer member 9 along the longitudinal direction of the retainer member 9 with a space provided therebetween. The engaging portions 15 and 17 are formed so as to have apertures in the same direction. Accordingly, the engaging portions 15 and 17 are each formed into semicircular shapes corresponding to diameters of the pair of rods 7A and 7B. Moreover, fixing screws 19 are screwed in the vicinity of the apertures of the engaging portions 15 and 17, and tip portions (lower end portions) of the fixing screws 19 are formed into tapers which provide taper faces 21 so that the tip portions can freely abut on outer peripheries of the rods 7A and 7B engaged with the engaging portions 15 and 17.

In the above-described constitution, the retainer member 9 of the vertebral body retainer 1 is disposed between the spinous processes 5 each existing on the adjacent vertebral bodies 3, and the spinous processes 5 are abutted on the abutting portions 11 provided on the both sides of the retainer member 9. Moreover, the engaging portions 15 and 17 provided on the retainer member 9 are engaged with the pair of rods 7A and 7B disposed on the both sides of the spinous processes 5, and then the fixing screws 19 are tightened. In this way, the rods 7A and 7B, and the retainer member 9 are integrated.

When the pair of rods 7A and 7B is integrated with the retainer member 9 as described above, the distance between the rods 7A and 7B are retained constantly by the retainer member 9, and movements of the rods 7A and 7B are thereby controlled. In other words, in the state where the both end portions of the rods 7A and 7B are fixed to the spaced vertebral bodies 3 with the implants such as a plurality of screws provided therebetween, the retainer member 9 is fixed to the rods 7A and 7B.

Therefore, the vertebral bodies 3 in the spaced positions are retained in the constant distance with the rods 7A and 7B fixed thereto, and the distance between the spinous processes 5 located on the both sides of the retainer member 9 are controlled by the retainer member 9. Accordingly, movements of the vertebral bodies 3 toward a mutually approaching direction are controlled. Moreover, in the state where the blades provided on the both side portions of the retainer member 9 bite slightly into the spinous processes 5, relative movements of the adjacent spinous processes 5 are restricted, whereby displacement of the vertebral bodies 3 is effectively controlled.

Moreover, when the rods 7A and 7B are fixed to the engaging portions 15 and 17 by tightening the fixing screws 19, the rods 7A and 7B are tightly pressed into the engaging portions 15 and 17 by wedge effects of the taper faces 21 provided on the fixing screws 19. Furthermore, the fixing screws 19 are located in the positions which are shifted inward from the central axes of the rods 7A and 7B, i.e. toward the aperture sides. Hence, the taper faces 21 provided on the tip portions of the fixing screws 35 abut on the outer peripheries of the rods 7A and 7B when the fixing screws 35 are tightened and act to press the rods 7A and 7B obliquely downward. Accordingly, the rods 7A and 7B can be surely fixed by pressure into inner peripheries of the engaging portions 15 and 17. In addition, the tip portions of the fixing screws 19 narrow the apertures of the engaging portions 15 and 17, whereby the rods 7A and 7B can be surely fixed to the engaging portions 15 and 17.

Furthermore, in the above-described constitution, the engaging portions 15 and 17 provided on the retainer member 9 have the apertures in the same direction. Therefore, it is possible to engage and detach the engaging portions 15 and 17 to and from the pair of rods 7A and 7B simultaneously. In this way, engagement and detachment can be facilitated.

As will be understood from the foregoing description, according to the present invention, the retainer member disposed between the spinous processes can be fixed integrally to the pair of rods disposed on the both sides of the spinous processes. Moreover, it is possible to allow the blades provided on the both sides in the width direction of the retainer member to bite into the spinous processes. Therefore, the distance between the spinous processes can be stably retained while controlling movements of the spinous processes, whereby the problem of the proposed art as described above will be satisfactorily resolved.

The entire content of a Japanese Patent Application No. P2002-32752 with a filing date of Feb. 8, 2002 is herein incorporated by reference.

Although the invention has been described above by reference to certain embodiments of the invention, the invention is not limited to the embodiments described above will occur to these skilled in the art, in light of the teachings. The scope of the invention is defined with reference to the following claims.

What is claimed is:

1. A vertebral body distance retainer, comprising:
    a retainer member including engaging portions that engage a pair of rods,
    the retainer member comprising generally parallel side surfaces having abutting portions provided with sharp blades projecting in opposite directions from each generally parallel side surface, the abutting portions engaging a plurality of adjacent vertebral bodies and freely abut spinous processes of the adjacent vertebral bodies,
    wherein a first distance extending generally perpendicular to respective edges of the oppositely projecting sharp blades is larger than a second distance extending generally perpendicular to the generally parallel side surfaces,
    wherein the oppositely projecting sharp blades are provided at least at a center of the retainer member with respect to a longitudinal extending direction of the retainer member,
    wherein the respective edges of the oppositely projecting sharp blades are formed having a sharp angle, and
    wherein the sharp angle is positioned intermediate a distance defined between opposing planar surfaces, the opposing planar surfaces intersecting the parallel side surfaces;
    fixing screws which fix the pair of rods to the engaging portions; and
    the vertebral body distance retainer being disposed between the spinous processes of the adjacent vertebral bodies, so that a distance between the spinous processes is maintained.

2. The vertebral body distance retainer of claim 1, wherein the fixing screws are provided with a taper face at a tip portion thereof, the taper face abutting an outer peripheral face of the pair of rods located in the engaging portions.

3. The vertebral body distance retainer of claim 1, wherein the fixing screws are located in a position shifted from a central axis of the rod engaged with the engaging portion toward an aperture of the engaging portions.

* * * * *